United States Patent
Stone et al.

(10) Patent No.: US 7,673,746 B2
(45) Date of Patent: Mar. 9, 2010

(54) RECYCLING CONTAINER FOR THE COLLECTION AND TEMPORARY STORAGE OF MERCURY CONTAMINATED WASTES IN DENTAL FACILITIES

(75) Inventors: Mark E. Stone, Wilmette, IL (US); Ronald S. Karaway, Kenosha, WI (US); Denise L. Berry, Gurnee, IL (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 93 days.

(21) Appl. No.: 12/103,112

(22) Filed: Apr. 15, 2008

(65) Prior Publication Data
US 2008/0257759 A1    Oct. 23, 2008

Related U.S. Application Data

(60) Provisional application No. 60/925,908, filed on Apr. 20, 2007.

(51) Int. Cl.
*B65D 85/84* (2006.01)
(52) U.S. Cl. .................. 206/63.5; 206/524.3; 206/524.4
(58) Field of Classification Search .................. 206/366, 206/438, 439, 63.5, 524.1, 524.3, 524.4, 206/524.5, 524.6; 220/495.01
See application file for complete search history.

(56) References Cited

U.S. PATENT DOCUMENTS

| 3,752,065 A * | 8/1973 | Reiter | 100/123 |
| 4,160,323 A * | 7/1979 | Tracy | 433/77 |
| 4,362,241 A * | 12/1982 | Williams | 206/210 |
| 2006/0093990 A1 * | 5/2006 | Stone et al. | 433/92 |
| 2008/0053883 A1 * | 3/2008 | Darcy et al. | 210/188 |

* cited by examiner

*Primary Examiner*—Jacob K Ackun, Jr.
(74) *Attorney, Agent, or Firm*—Joseph K. Hemby, Jr.; Ning Yang

(57) ABSTRACT

The present invention is directed to a container for the collection and temporary storage of amalgams and other mercury wastes. The container can include a hollow body with air-tight lid, and one or more mercury sorbents contained in a filter bag. The filter bag covers the inside surface of the hollow body and has holes that allow air exchange between the air in the hollow body and the sorbents. As air exchange occurs, mercury vapors released from dental wastes binds to the mercury binding materials. A self-closing door was made on the lid, which automatically closes after each waste disposal.

19 Claims, 5 Drawing Sheets

RECYCLING CONTAINER FOR THE COLLECTION AND TEMPORARY STORAGE OF MERCURY CONTAMINATED WASTES IN DENTAL FACILITIES

CROSS-REFERENCES TO RELATED APPLICATIONS

This application claims priority to U.S. Provisional application 60/925,908, filed Apr. 20, 2007 and is hereby incorporated by reference.

BACKGROUND

1. Field of Invention

The present invention relates to the collection and temporary storage of mercury contaminants, more specifically the collection and temporary storage of used dental amalgam in a treatment facility.

2. Description of the Prior Art

Mercury is a unique metal in that it has an exceptionally high vapor pressure of 0.001201 torr at 20° C., which corresponds to a saturation concentration in air of 13.2 mg/m$^3$. Table 1 shows the Hg concentrations in air increase rapidly with increasing temperature. At 20° C., the saturation concentration of Hg in air is 132 times the OSHA permissible exposure limit.

TABLE 1

Vapor pressure and saturation concentrations of mercury in air at selected temperatures.

| Temperature, ° C. | Temperature, ° F. | Vapor Pressure (torr) | Hg Concentration, mg/meter$^3$ |
| --- | --- | --- | --- |
| 0 | 32 | 0.000185 | 2.2 |
| 10 | 50 | 0.000490 | 5.9 |
| 20 | 68 | 0.001201 | 13.2 |
| 30 | 86 | 0.002777 | 29.5 |
| 40 | 104 | 0.006079 | 62.6 |

The high vapor pressure of mercury can result in mercury vapor concentrations that exceed both Occupational Safety and Health Administration (OSHA) and The National Institute for Occupational Safety and Health (NIOSH) exposure limits if stored at room temperature. The current OSHA permissible exposure limit (PEL) for mercury vapor is 0.1 milligram per cubic meter of air (mg/m$^3$) as eight-hour time weighted average (TWA). National Institute for Occupational Safety and Heath Recommended Exposure Limit (REL) for Hg vapor is 0.05 mg/meter$^3$ for up to a 10-hour workday and 40-hour workweek. American Conference of Governmental Industrial Hygienists (ACGIH) has an Hg threshold limit value (TLV) of 0.025 mg/meter$^3$ as a time-weighted average for an 8-hour workday and a 40-hour workweek (Occupational Safety and Health Guideline for Mercury Vapor, Dept. of Labor, http://www.osha.gov/SLTC/healthguidelines/mercuryvapor/recognition.html. 7 Mar. 2007).

TABLE 2

Human exposure limits to elemental Hg vapor from OSHA, NIOSH, and ACGIH.

| | Type of Limit | Inorganic Hg Compounds |
| --- | --- | --- |
| Federal OSHA[a] | 8-Hour TWA | 0.1 mg/meter$^3$ (100,000 ng/meter$^3$) |
| NIOSH[b] | 8-Hour TWA | 0.05 mg/meter$^3$ (50,000 ng/meter$^3$) |
| ACGIH[c] | 8-Hour TWA | 0.025 mg/meter$^3$ (25,000 ng/meter$^3$) |

An amalgam is any mixture of mercury with another metal or an alloy, such as silver, tin, copper, and zinc (Webster's New College Dictionary. Houghton Mifflin Company. 2001). Cadmium, indium, palladium, and lead were historically used in some amalgam products. However, modern low-copper amalgams typically have a powder component composed of 69.4% silver, 3.6% copper, 26.2% tin, and 0.8% Zinc, they have a liquid component of 42% to 45% mercury by weight. Mercury amalgams are commonly used in dentistry because they are cheap, easy to use, durable, and regarded as safe. Although, for modern dentists who are exposed to mercury amalgam and vapor on a daily basis, no evidence of mercury poisoning have been demonstrated, some studies have shown that mercury from amalgams does affect dentists mildly. In several large-scale studies, dentists were asked to perform several cognitive and behavioral tests. Their tests results were compared to those of a normal population. The dentists lagged behind the normal population in many areas. In one study, 14% of dentists received worse scores in memory, coordination, motor speed, and concentration when exposed to an average personal air concentration time weighted average (TWA) [1]. A UK study that examines the health effects of mercury on 180 dentists, has found that the dentists who participated in the study had urinary mercury excretion levels four times of that of the control group on average. Dentists were significantly more likely than control subjects to have disorders of the kidney or memory disturbance [2].

Mercury from improperly disposed amalgam may be released into the air and sewage water. In various countries, amalgam removed from teeth is classified as hazardous waste. Environmental risks are mitigated provided that amalgams are disposed of properly. The American National Standards Institute with the American Dental Association issued a standard regarding the proper handling and disposal of amalgam waste [3].

Prior to this invention, amalgam waste, including unused amalgam would be temporarily stored in containers that could be tightly sealed to prevent the escape of mercury vapor. Normally, screw top high-density polyethylene containers are used for the collection of used amalgam capsules and other mercury contaminated wastes, such as contact and non-contact amalgam scraps, and used chair side traps. However, technicians in the dental facilities often leave the recycling containers open, causing mercury vapor to be released into the dental treatment room.

U.S. Pat. No. 4,698,018 by Nepault discloses a device for collecting dental amalgam, designed to prevent amalgam spills. In operation, a collection cup is allowed to rotate in only one direction, and disposes waste amalgam from the cup into a waste cylinder as it reaches the inverted position. The cup will automatically return to its original upright position after release of pressure. This device eliminates the need to close the waste container manually after each disposal, thus reduces the possibility of exposing the amalgam waste directly to open air. However, this device does not prevent mercury vapor from forming within the container during storage and does not have mechanisms to impede or prevent the mercury vapor from leaking into the treatment facility Many materials can bind elemental mercury or mercury oxide. Scientist and engineers have tried to use these materials to remove mercury-containing waste from air or gas streams. For example, U.S. Pat. No. 6,719,828 by Lovell et al. disclosed a silicate based sorbent, used to absorb elemental mercury or oxidized mercury species such as mercuric chloride from a flue gas (e.g., $SO_2$, NO, $NO_2$, and HCl). This sorbent is prepared by first generating an exchange silicate substrate via ion exchange between a phyllosilicate substrate, such as vermiculite or montmorillonite, and a solution containing one or more groups of polyvalent metals such as tin, iron, titanium, manganese, zirconium and molybdenum, dissolved as salts. The sorbent is then made by adding sulfide ions to the exchanged silicate substrate in a controlled manner.

Flyash has also been used to remove mercury from streams of waste gases, U.S. Pat. No. 4,273,747 by Rasmussent and U.S. Pat. No. 4,273,747 by Knowles. Flyash is usually composed of common oxygenated inorganic compounds such as silica, aluminum, calcium, magnesium, iron, sodium, potassium, titanium, and sulfur. Aluminosilicate and calcium compounds often account for 80% of the mass. Because of the larger surface area per unit mass yield, flyash often acts as a sorbent for extremely fine particulates, fumes, or vapor phase species. U.S. Pat. No. 5,787,823 by Knowles teaches that largely anhydrous flyash has abilities to absorb gases or fumes such as vapor phase mercury from waste gas streams. Knowles also teaches that this ability of flyash is not dependent upon the flyash location with respect to the gas stream. Flyash, which is normally borne by the combustion gas stream, can be expected to absorb mercury at rates similar to flyash that is concentrated on the surface of a filter bag as a filter cake. This is because flyash, which is part of the filter cake, is very loosely bonded to other flyash particles, and forms a very porous mass. The exposed and available surface area for reactions of individual flyash particles in such a filter cake approximates the same as an individual flyash particle which is airborne. Particles ranging in size from about 1.0 µm to about 100 µm that are largely composed of aluminosilicate mineral phases, can also be used to capture mercury in a gas stream because the large surface area per particle due to porosity.

Modified active carbon, nano-materials and polymers have also been studied as mercury sorbent. US patent application by Olson et al. (US Pub. No. 2006/0048646) describes a sorbent made of active carbon modified by reaction with a halogen and/or halide promoter, which binds mercury. Others have experimented with nanocomposites that combines high-surface silica with photocatalytic properties of Titania for effective capture of elemental mercury vapor [4]. Another example of a mercury-binding sorbent is Vinylpyridine copolymer which showed a greater than 90% removal efficiency [5].

SUMMARY OF INVENTION

It is an objective of the current invention to provide a recycling container for the collection and temporary storage that prevents or reduces the release of mercury vapor into the storage/treatment facility atmosphere.

Another objective of this invention is to provide a temporary collection container that automatically closes after each disposal, thus preventing mercury vapor from leaking from the container.

A further objective of this invention is to provide a temporary storage container that prevents mercury vapor from forming within the container from dental mercury waste at room temperature.

Yet another objective of this invention is to provide a recycling container for the collection and temporary storage of mercury waste in a dental office that is both cost-effective and convenient to use.

DETAILED DESCRIPTION OF THE INVENTION

The current invention is designed for the collection and temporary storage of mercury containing dental wastes in a treatment facility. The inventive device prevents or reduces the release of mercury vapor from a dental waste container into the treatment or office atmosphere.

The container of the present invention comprises a hollow body fitted with an air-tight lid and a filter bag which contains at least one mercury-binding material. An opening was made on the lid and sealed by a self-closing door. This self-closing door allows easy placement of dental waste into the container, and automatically seals the container after each waste disposal. In operation, the self-closing door will open under pressure allowing the operators to discard mercury containing wastes into the container. After waste disposal, the pressure was released and the door will automatically close. This prevents mercury vapor from being released into the storage or treatment room. A quilted filter bag containing at least one mercury sorbent is fitted onto the inside surface of the container to trap any mercury vapor released from mercury containing dental waste.

Figure 1:
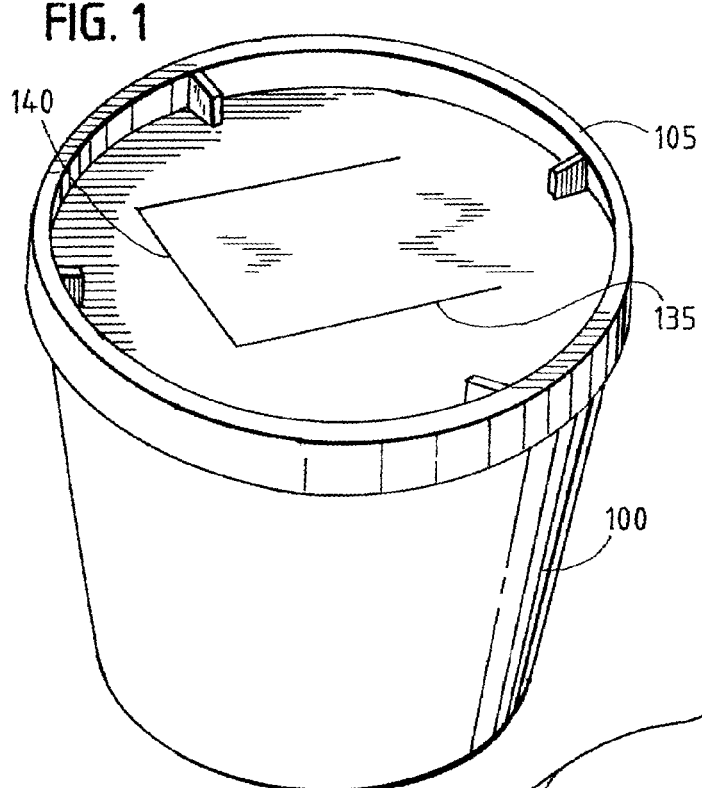
FIG. 1 is a perspective view of one embodiment of the recycling container.
Figure 2:
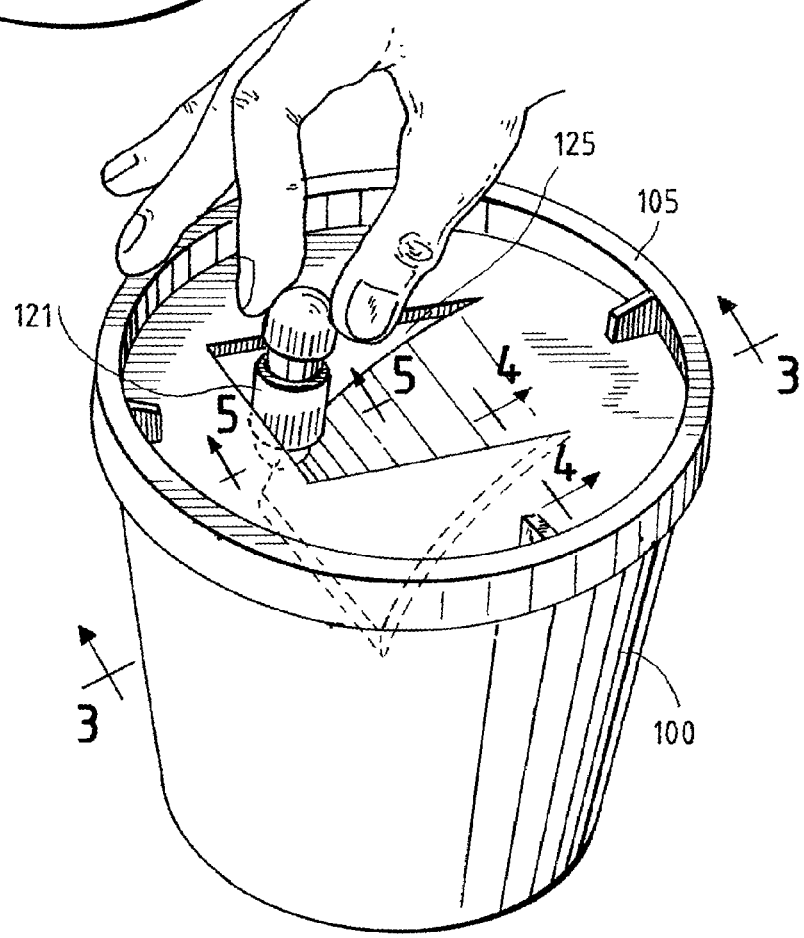
FIG. 2 is a perspective view of the illustrating the operation of the embodiment of FIG. 1.
Figure 3:
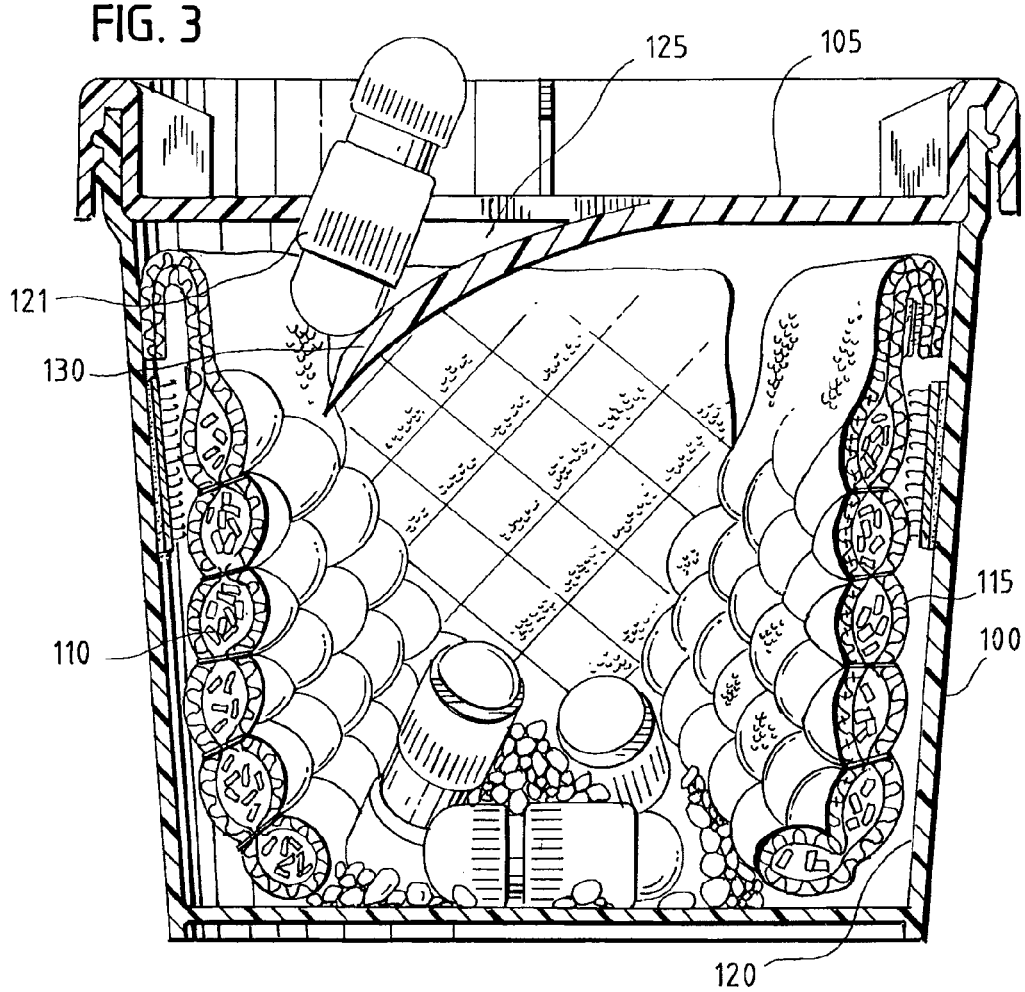
FIG. 3 is a cross-sectional view of the embodiment of the recycling container as shown on FIG. 1.
Figure 4:
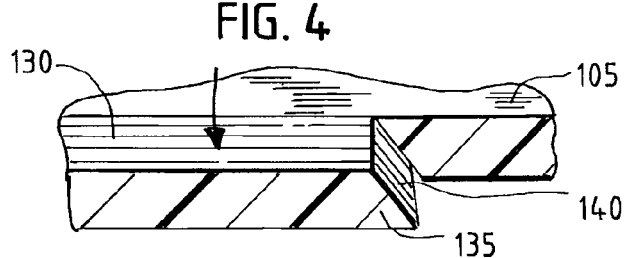
FIG. 4 is a cross-sectional view showing an embodiment of the self-closing door.

As illustrated in FIG. 1, a container of this invention comprises a hollow body 100 with a closed bottom and an air-tight lid 105. An opening 125 is made on the lid 105 to allow mercury containing dental waste 121 to be disposed into the container (FIG. 2). This opening 125 is sized to allow easy placement of wastes and is sealed during storage to minimize mercury vapor leakage. A self-closing door 130 is operatively connected to the lid 105 to automatically seal the opening 125 after each deposit, in turn, preventing the operator from unintentionally leaving the container open (FIG. 3)

Figure 5:
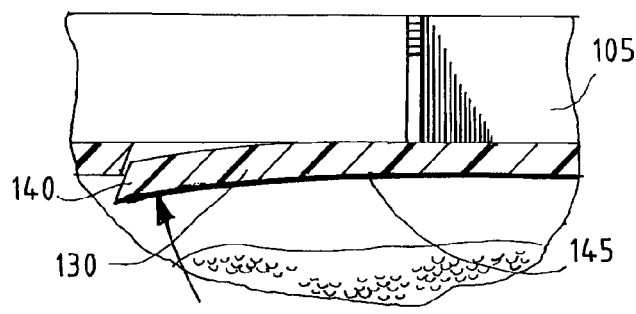
FIG. 5 is a cross-sectional view of the embodiment shown in FIG. 4, showing door is closing.
Figure 6:
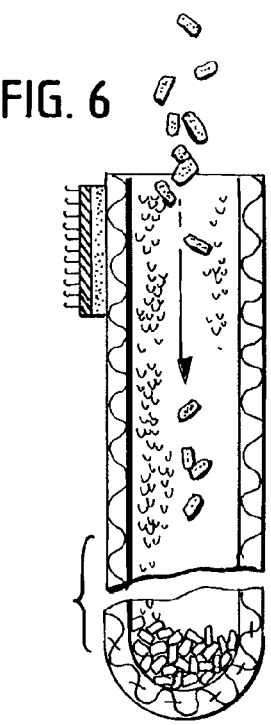
FIG. 6 is a cross-sectional view of an embodiment of the filter bag.

A preferred embodiment of the recycling container is shown in FIG. 1-5, a rectangular self-closing door 130 may be created from the lid by making two perpendicular cuts 135 along the rectangle's longer sides and an angled cut 140 at one of its short end (FIG. 2). In operation, the self-closing door 130 opens into the container under a downward pressure (FIG. 2 and FIG. 4), allowing the operator to place a dental waste into the container. After being released, the self-closing door 130 springs back and automatically reseals the container (FIG. 5). In this embodiment, the air-tight lid 105 is made of a semi-flexible material, which is capable of bending under pressure and straightens back after releasing such pressure. Examples of such material include, but are not limited to, thick sheet of latex or rubber. The angled cut 140 at the door's short end ensures an adequate seal of the opening, and reduces mercury vapor leakage from the container.

Figure 7A:
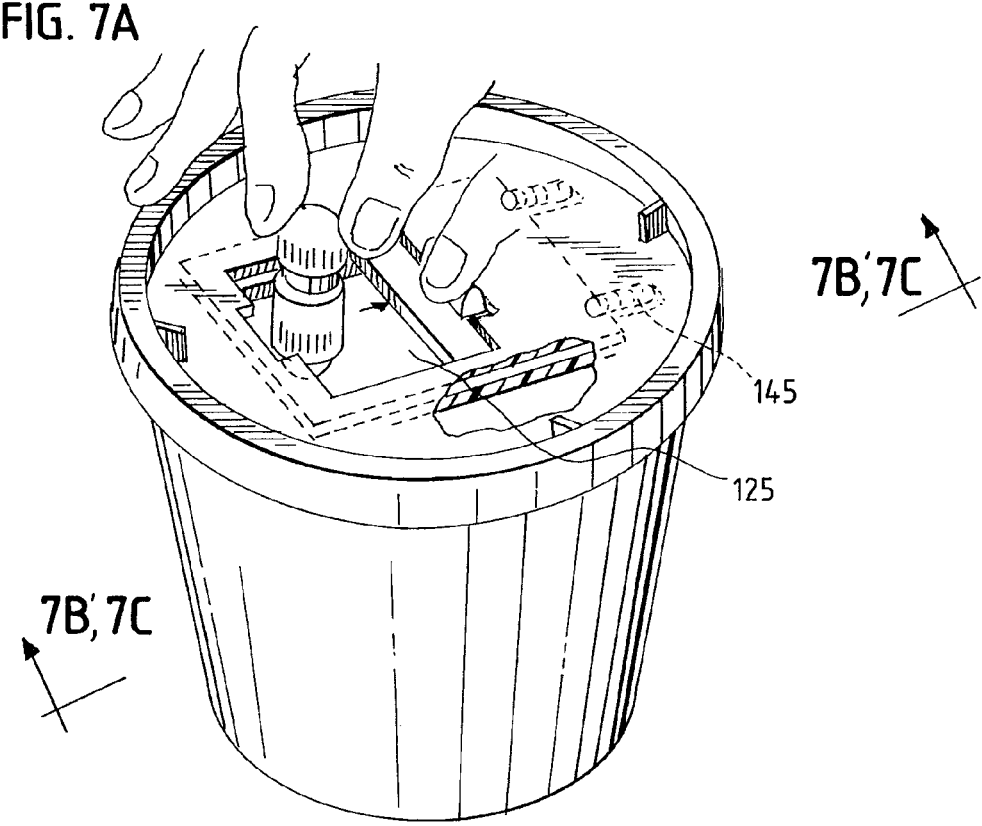
FIG. 7A is a perspective view of an embodiment of recycling container, showing a spring operated self-closing door.
Figure 7B:
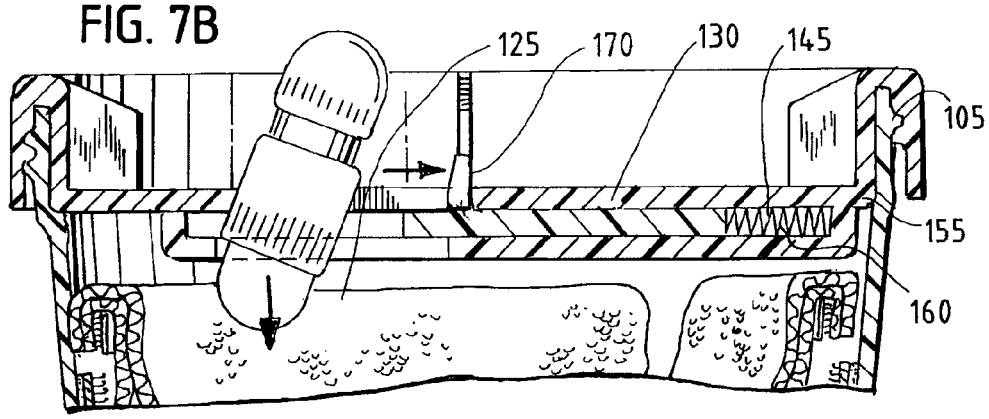
FIG. 7B is a cross-sectional view of the embodiment of FIG. 7B, showing the spring is being compressed.
Figure 7C:
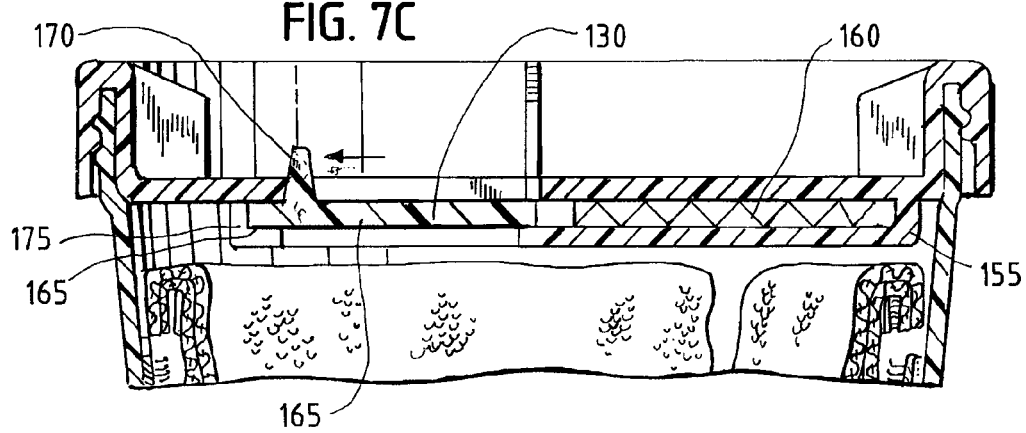
FIG. 7C is a cross-sectional view of the embodiment of FIG. 7B, showing the spring decompressing to close the door.
Figure 10:
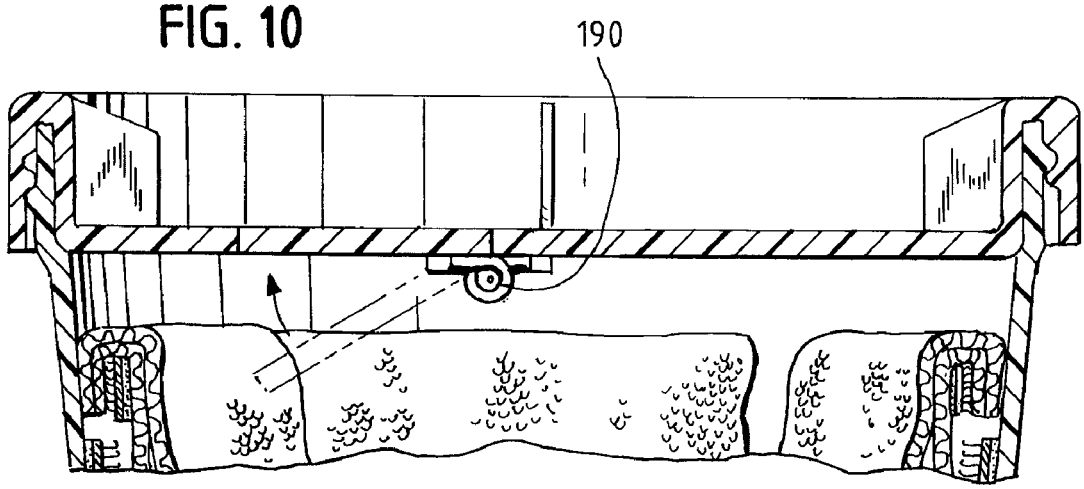
FIG. 10 is a cross-sectional view of a spring hinge operated self-closing door.

In an alternative embodiment, a spring 160 (FIG. 7A-C) or a spring hinge 190 (FIG. 10) is used to create a self-closing door. An example of a spring operated self-closing door is shown in FIG. 7. Referring to FIGS. 7B and C, one or more housing unit 155 is installed under the air-tight lid 105 next to the opening 125. A spring 160 resides inside each housing unit 155. A rectangular door 130 is operatively connected to the spring 160. For example, the rectangular door 130 is partially inserted into the housing unit 155 next to the spring. In operation, a technician opens the container by sliding the door into the housing unit, which in turn compresses the spring, which is shown in FIG. 7B. A handle 170 may be formed on the exposed portion 165 of the rectangular door, allowing easy grip of the door 130. Once a dental waste is deposited into the container, the technician releases the handle, and the spring decompresses, and pushes the door closed, thus sealing the opening (FIG. 7C). A stop 175 is formed under the lid opposite the spring, which stops the movement of the door when it fully closes the opening FIG. 7C. This stop may be made as part of the housing unit 175, which locks in the hidden portion of the door 165, to stop the door from further sliding when the opening is fully sealed.

Figure 9:
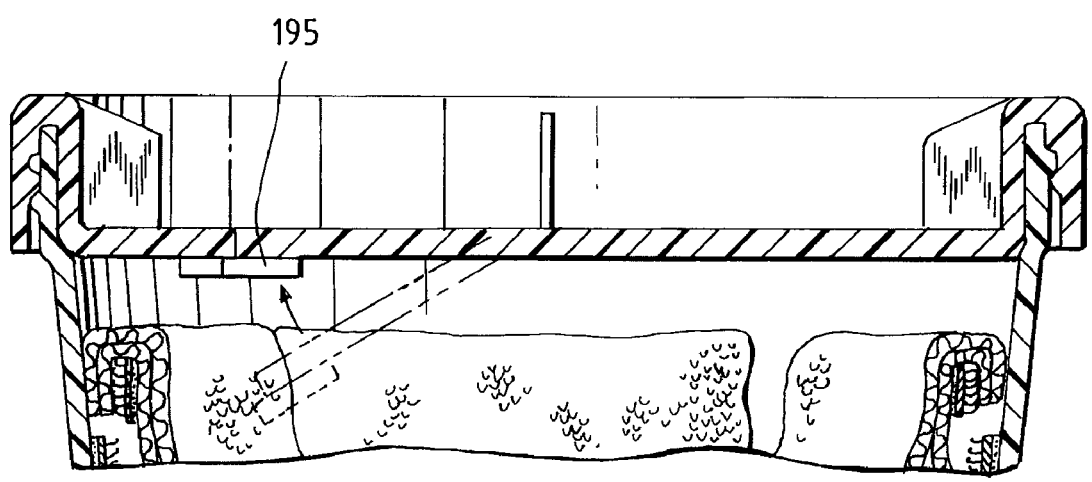
FIG. 9 is a cross-sectional view of a magnetic pair operated self-closing door.

Instead of a spring, magnetic pieces 195 may be used (FIG. 9) or a spring hinge 190 (FIG. 10) may be used to operate the self-closing door. In operation, the spring hinge 190 or magnetic pieces 195 automatically close the door after removal of pressure.

Figure 8A:
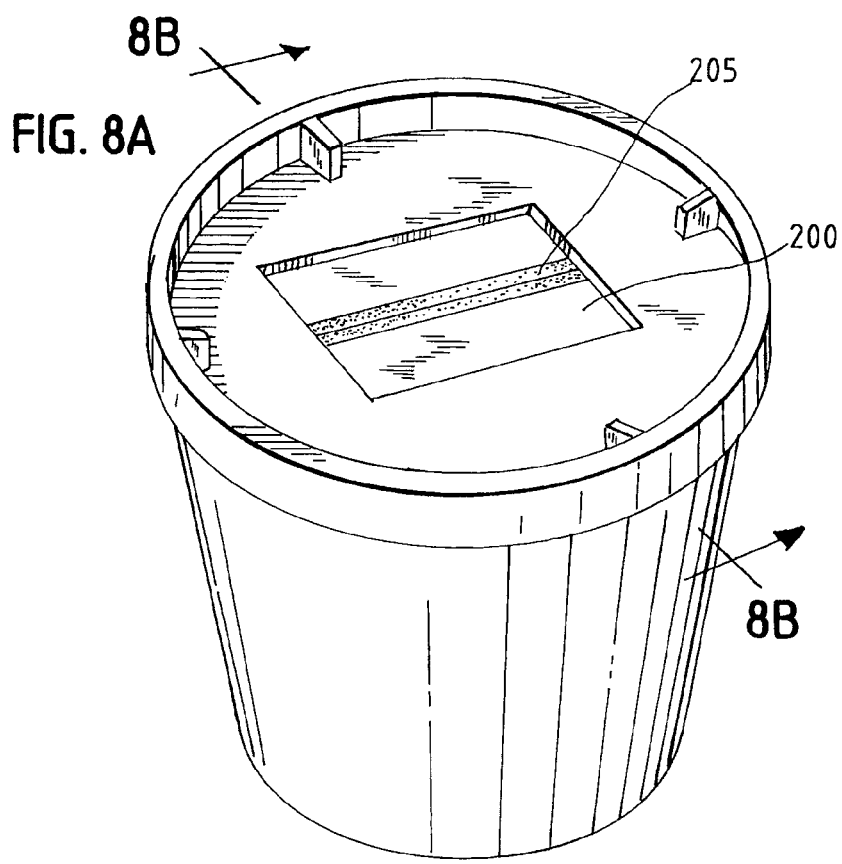
FIG. 8A is a perspective view of an embodiment of the recycling container, showing a film/string operated self-closing door.
Figure 8B:
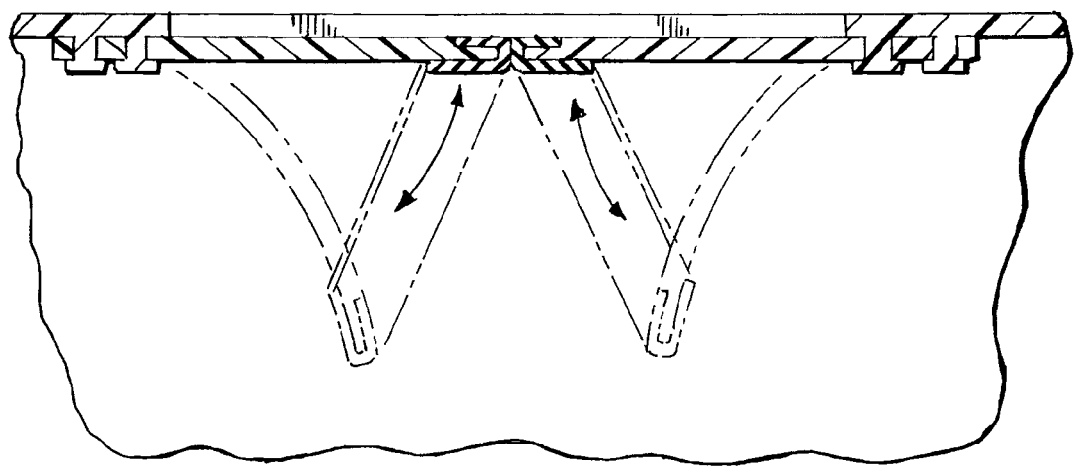
FIG. 8B is a cross-sectional view of a film/elastic bands operated self-closing door.

Yet another design of the self-closing door may be operated by film and elastic bands. As shown in FIGS. 8 A and B, the opening 125 may be covered by overlapping films 200. The two overlapping sheets of film 200 are attached to the side of the opening via mechanical, chemical or heat means. Elastic bands 205 may be installed on the overlapping end of the films. The films open when a pressure is applied to the elastic bands. With the release of that pressure, the elastic band draws the films back together and seals the opening FIG. 8B. The film may be made of any flexible material, preferably gas impermeable. Examples of such materials may include, but are not limited to plastic and rubber.

The hollow body 100 may be made of a gas impermeable material, such as tempered glass, plastic, fiber glass, metal, or metal alloys. Examples of plastic that may be used for the body of the container comprises of polyvinyl chloride, polyethylene, polypropylene and polystyrene. Additional sealing materials, such as rubber or latex, may be applied along the peripheral of door and/or the opening to provide a tighter seal of the opening.

In a preferred embodiment, the mercury-binding materials are sorbents, which is defined as a material that binds another material by adsorption or absorption. It is contemplated that any number of sorbent materials can be utilized in this invention, including activated carbon, metal oxide sorbent, sodium sulfide particles, and basic silicate or oxide sorbents.

Under a preferred embodiment of this invention, one or a combination of mercury-binding materials, such as mercury-binding sorbents, are housed on the inside surface of the container, as shown in FIG. 3. Depending on the form and shape of the mercury-binding materials, filter bags may be used to house these sorbents. The filter bags can be made of any suitable flexible materials, such as plastic, nylon, or any natural materials. The filter bag may be a mesh bag or a perforated bag, with holes sized both to hold the sorbents, and to provide easy air exchange between the sorbent and the container interior. As air exchange occurs, mercury vapor released by the mercury-containing wastes comes into contact with mercury-binding sorbent and is bound to the sorbent and trapped inside the filter bag. Mercury vapor is thus removed from the interior of the container. This in turn, reduces the mercury vapor concentration within the container, and prevents mercury vapor from leaking into the treatment room atmosphere when the container was opened to deposit waste.

The filter bag may be attached to the container via chemical or physical means. An example of a chemical attachment is by applying chemical adhesives to the inside surface of the container and the contacting surface of the filter bag. Velcro® strips, buttons, zippers and other similar mechanical means may also be used to attach the filter bags to the inside surface of the container. If the filter bag and the container are both made of plastic, filter bag may also be attached to the container via heat fusion.

In a preferred embodiment, the filter bag is quilted with each pocket containing a small amount of sorbents. An advantage of the quilted filter bag is that as wastes accumulated on the bottom of the container, sorbents will not be buried and thus have a continuously contact with any mercury vapor formed from the wastes.

The present invention aims to protect dental operatory personnel and patients from exposure to harmful mercury vapor by reducing its leakage from a collection and temporary storage container. However, the invention is not limited to this particular use. It may be used for the collection and storage of other materials that releases toxic vapors or gases under room temperature. Sorbents used for the other applications must bind to the particular toxic elements. They must also store safely in a container under room temperature.

Although the invention has been described and illustrated with respect to several embodiments, it is readily apparent that those skilled in the art will be able to make still other modifications of the exemplary ones without departing from the spirit and scope of the invention as defined in the appended claims.

EXAMPLE 1

Evaluation of Recycling Container Using Activated Carbon Sorbents

The sorbents used in this study are based on activated carbons, which include a wide range of amorphous carbonaceous materials that exhibit a high degree of porosity and extensive interparticulate surface area. The activation process increases the original porosity in the carbon and may involve treatment with carbon dioxide, steam (water vapor), zinc chloride, and phosphoric acid as well as hydroxides of alkali metals. The pores possess intense van der Waals forces (non-stable weak electromagnetic forces generated by momentary polarization of molecules; i.e., fluctuating dipoles). These forces are responsible for the adsorption process of activated carbon. Chemical modification of activated carbon can be used to create products with substantially improved Hg adsorption properties. The addition of sulfur to activated carbon increases its absorption capacity due to the chemisorption of Hg and formation of mercuric sulfide, HgS. An eleven percent (by weight) addition of sulfur to activated carbon increases the adsorption capacity by a factor of over 400.

Iodized activated carbon adsorbs Hg vapor 20-to-160 times more than untreated activated carbons with Hg vapor concentrations up to 40 mg/m$^3$.

Containers

A prototype amalgam waste-recycling container was fabricated by modifying commercially available two-gallon, high density polyethylene (HDPE) containers (M&M Industries Inc., Chattanooga, Tenn., USA) (see FIG. 3). Sampling ports were placed in uniform locations in all forty prototype containers used in this study. The containers were equipped with lids possessing integrated gaskets. Sealing ability of the containers was evaluated by filling them with water and storing them upside down overnight. The containers were checked for leaks the following morning. No leaks were found.

Sorbents

Four different sorbents were evaluated: activated carbon, AC (Serfilco, Inc., Northbrook, Ill. USA), activated carbon impregnated with sulfur, GC-IPSp (General Carbon Corp., Paterson, N.J. USA), activated carbon mixed in the lab with sublimed iodine, AC-SI (5 g of sublimed iodine crystals mixed with 200 g activated carbon), and activated carbon impregnated with iodine crystals, GC-II (General Carbon Corp., Paterson, N.J. USA). Eight containers were used for each testing groups. Ten (10) grams of ground and sieved amalgam with particle size range from 210-to-710 m were placed into each testing containers. Two hundred (200) grams of sorbent were put into two mesh bags, which were attached to the inside wall of thirty-two containers with loop-and-hook fasteners. The eight containers from the control group had no sorbents placed inside.

Sampling Schedule and Hg Vapor Instruments

Containers were sampled in random order with measurements taken Tuesday through Friday at 7 AM for four weeks using either OhioLumex RA-915+™ Hg vapor analyzer (baseline and treatment samples) or Arizona Instruments Jerome 431-X™ (control samples). Baseline Hg vapor levels were determined for each container prior to placement of amalgam. The RA-915+™ Hg vapor analyzer (OhioLumex, Twinsburg, Ohio, USA) uses differential Zeeman atomic absorption spectrometry with high frequency modulation of polarized light (253.7 nm) in a multi-path optical cell (10 meters) to measure Hg vapor with a vendor-claimed detection limit of ng/meter$^3$. The "protocol mode" of the RA-915+™ analyzer was used to measure the Hg concentrations. In this mode, three measurements over a ten-second sampling period (frame time) are taken and the mean and relative deviation is reported by the instrument. The Jerome 431-X™ analyzer (Arizona Instruments LLC., Tempe, Ariz., USA) was used to measure Hg vapor levels in the control containers (no sorbent). This instrument measures Hg vapor indirectly by drawing a precise volume of air over a gold foil sensor. When the instrument is activated, 750 cubic centimeters of air/minute are drawn into the analyzer and through a filter to remove acidic gases (which interfere with the analysis). Air then flows past a gold foil sensor and the Hg in the air sample adsorbs to the gold foil causing a change in electrical resistance. The electrical resistance in the sensor increases proportionally with increasing mass of Hg. The detection limit for the Jerome 431-X™ is 3000 ng/meter$^3$. At the start and the end of each sampling day the Jerome 431-X™ was regenerated and "zeroed" as required by the manufacturer.

Results

Table 3 shows weekly means in nanograms of Hg per cubic meter (ng/meter$^3$) of air. Over the four-week span of the testing period, the Hg vapor levels generally decreased and differences between groups decreased.

TABLE 3

Control group and weekly mean concentrations of Hg vapor in units of ng/meter$^3$.

| Group | Baseline Hg | Week 1 | Week 2 | Week 3 | Week 4 |
|---|---|---|---|---|---|
| Control | 87 | 667,531 | 266,438 | 130,625 | 92,125 |
| AC | 86 | 230 | 96 | 74 | 54 |
| GC-IPSp | 76 | 153 | 65 | 52 | 43 |
| AC-SI | 78 | 45 | 33 | 41 | 36 |
| GC-II | 74 | 55 | 46 | 43 | 40 |

Activated carbon (AC); activated carbon impregnated with sulfur (GC-IPSp); activated carbon mixed in the lab with sublimed iodine (AC-SI); activated carbon impregnated with iodine crystals (GC-II)

Mean removal efficiencies at Week 1 were calculated to be 99.97%, 99.98%, 99.99% and 99.99% for AC, GC-IPSp, AC-SI, and GC-II, respectively. Control data were not included in any of the statistical analysis. A 2-way ANOVA (group by week) had significant main effects and interaction. 1-way ANOVA's were significant at baseline and weeks 1 and 2; post-hoc Tukey ($p \leq 0.05$) groupings are reported in the Table 4.

TABLE 4

Tukey post-hoc groupings ($p \leq 0.05$) are shown below for week one and week two. After the second week the differences between the means of the four groups were not statistically significant. Groups with the same letter within a column are not significantly different.

| Group | Baseline Hg | Week 1 | Week 2 |
|---|---|---|---|
| AC[1] | A | A | A |
| GC-IPSp[2] | A, B | A | B |
| AC-SI[3] | A, B | B | B |
| GC-II[4] | B | B | B |

The concentrations of Hg in dental amalgam waste containers can be substantial, even saturating the gold foil sensor in the Jerome 431-X™ Hg vapor analyzer (Hg vapor concentrations greater than 0.999 mg/m$^3$ were routinely measured in one clinical location). These dramatically elevated Hg vapor concentrations have been measured in containers with scrap amalgam and in containers storing spent amalgam capsules.

At week one of sampling, activated carbon, and sulfur-impregnated activated carbon removed less Hg than activated carbon mixed with sublimed iodine crystals or activated carbon impregnated with iodine. At week two, all three of the modified activated carbon products removed more Hg vapor than the activated carbon alone. However after week three, there was no statistical difference between the four products.

The four activated carbon sorbents evaluated in this project were all successful in dramatically reducing Hg vapor levels in containers loaded with 10 g of ground and sieved amalgam particulate. This study demonstrated that low-cost carbon based sorbents can dramatically reduce Hg vapor levels and can be a valuable component of dental amalgam waste recycling containers.

REFERENCES

1. Ngim, C H, Foo S C, Boey K W, Jeyaratnam J (November 1992). "Chronic neuronbehavioral effects of elemental mercury in dentists". Br J Ind Med. 49 (11): 782-90. PMID: 1463679.

2. K. A. Ritchie et al. Health and neuropsychological functioning of dentists exposed to mercury. Occupational and Environmental Medicine 2002; 59:287-293.
3. ANSI/ADA No. 109.
4. Erik Pitoniak et al. Adsorption Enhancement Mechanisms of Silica-Titania Nanocomposites for elemental Mercury Vapor Removal. Environ. Sci. Technol., 39(5), 1269-1274, 2005.
5. Shaglaeva et al. Divinyl Sulfide-4-Vinylpyridine Copolymer as an Effective Sorbent for Mercury N. S. Russian Journal of Applied Chemistry Volume 78, Number 8/August, 2005. pp 1273-1275.

We claim:

1. A container for collection and temporary storage of mercury contaminated dental waste comprising:
   (a) a hollow body having a closed bottom and an air-tight lid, wherein said air-tight lid having an opening that is sealable by a self-closing door; and
   (b) at least one mercury-binding material, wherein said mercury-binding material is housed in a filter bag covering the inside surface of said hollow body, and said mercury-binding material is communicative with inside of said body.

2. The container of claim 1, wherein said mercury-binding material comprises a mercury-binding sorbent.

3. The container of claim 2, wherein said mercury-binding sorbent is selected from the group consisting of:
   (a) active carbon;
   (b) sulfur impregnated activated carbon
   (c) metal oxide sorbent;
   (d) sodium sulfide particles;
   (e) basic silicate sorbents;
   (f) modified silicate sorbents;
   (g) a flyash;
   (h) a silica-titania nanocomposite;
   (i) a polymer sorbent; and
   (j) a combination thereof.

4. The container of claim 1, wherein said self-closing door opens under pressure and automatically closes after releasing said pressure.

5. The container of claim 1, wherein said self-closing door is operatively connected to the lid using:
   (a) a spring;
   (b) a spring hinge; or
   (c) a flexible material.

6. The container of claim 1, wherein said filter bag is quilted with packets filled with said mercury-binding material.

7. The container of claim 1, wherein said filter bag is attached to the inside surface of said body by:
   (a) chemical adhesion;
   (b) mechanical means; or
   (c) heat fusion.

8. The container of claim 1, wherein said filter bag is a mesh bag, with holes sized to hold said mercury-binding material and to allow air-exchange between said mercury-binding material and the internal air said hollow body.

9. The container of claim 1, wherein said filter bag is a perforated, with holes sized to hold said mercury-binding material while allowing air-exchange between said mercury-binding material and the internal air said hollow body.

10. The container of claim 7, wherein said mechanical means comprises velcro, zipper, button or hook/hole assembly.

11. The container of claim 1, wherein said hollow body is made of a gas impermeable material.

12. The container of claim 11, wherein said gas impermeable materials is selected from the group consisting of:
    (a) tempered glass;
    (b) plastic;
    (c) fiber glass; and
    (d) metal or metal alloys.

13. The container of claim 1, wherein said air-tight lid is made of a flexible material.

14. The container of claim 1, wherein said opening is rectangular.

15. The container of claim 13, wherein said self-closing door is cut from the lid.

16. The container of claim 1, wherein a sealing material is applied to the edge of the air-tight lid and the hollow body.

17. The container of claim 16, wherein said sealing material comprises latex and rubber.

18. The container of claim 1, wherein sealing material is applied on the periphery of the self-closing door.

19. The container of claim 18, wherein sealing material comprises latex and rubber.

* * * * *